United States Patent [19]

Webster

[11] 4,282,182
[45] Aug. 4, 1981

[54] PACKAGE SAMPLING SYSTEM

[75] Inventor: Milo E. Webster, Braintree, Mass.

[73] Assignee: Instrumentation Laboratory Inc., Lexington, Mass.

[21] Appl. No.: 142,463

[22] Filed: Apr. 20, 1980

[51] Int. Cl.³ .......................... G01N 1/10; G01N 1/24
[52] U.S. Cl. .................................... 422/68; 73/864.23;
    422/100; 422/103; 422/83; 422/50
[58] Field of Search ........................ 422/63, 50, 68, 83,
    422/100, 103; 73/421 R, 421.5 R, 425.6

[56] References Cited
U.S. PATENT DOCUMENTS 4,120,662  10/1978  Fosslein ........................... 422/100 X

OTHER PUBLICATIONS

"Zahm Practical Testing Instruments," Zahm & Nagel Co., Inc., 74 Jewett Ave., Buffalo, N.Y., 1978 pp. 1–30.
"IL 307 Head Space Oxygen Analyzer Literature," Instrumentation Laboratory Inc., Sensorlab Division, 113 Hartwell Ave., Lexington, Ma. 02173.

Primary Examiner—Ronald Serwin

[57] ABSTRACT

Apparatus for analyzing the contents of a sealed package includes a package alignment assembly, and a probe assembly that has a puncturing tip. The package alignment assembly includes a positioning support surface in alignment with the puncturing tip and supplemental resiliently supported structure spaced from the support surface for aligning the package to be analyzed with the probe assembly. A flow path extends from the puncturing tip to an analysis unit for withdrawing and analyzing a sample of the contents of the package.

16 Claims, 12 Drawing Figures

PACKAGE SAMPLING SYSTEM

This invention relates to analysis apparatus, and more particularly to apparatus for analyzing contents of sealed packages.

It is frequently desirable to monitor or sample the contents of sealed packages. Products such as foods and drugs are easily oxidized, and residual oxygen in the packaging of such products can drastically reduce shelf life affecting quality, taste or product potency. For these reasons, such products are frequently packaged in containers that have been flushed with an inert gas to eliminate oxygen. Analyzers have been designed to sample both hard packages and soft packages after they have been filled and sealed and analyze either the packaged product or the head space gas above and surrounding the packaged products, using analysis techniques such as gas chromotography, paramagnetic techniques, and polarographic techniques. In a polarographic instrument, for example, the package is pierced and a small volume of the head space gas is drawn into an analysis cuvette for measurement. Dissolved oxygen and carbon dioxide values are routinely measured in the brewery industry as quality control parameters. Such products are typically hard packaged (in cans, bottles or the like). The configuration of hard package containers varies and the analysis apparatus desirably will readily accommodate a wide range of package configurations for sampling purposes. In analysis of the contents of either hard or soft packages, it is important to perform the analysis without contamination and with minimal distortion of the actual conditions within the sealed package to be analyzed.

In accordance with one aspect of the invention there is provided apparatus for analyzing the contents of a sealed package that includes a package alignment assembly, and a probe assembly that has a puncturing tip portion for puncturing the wall of a package on the alignment assembly. The package alignment assembly includes a support surface with an aperture therein for positioning the wall of the package to be punctured in alignment with the puncturing tip portion of the probe assembly, and alignment structure resiliently supported in spaced relation to the support surface for positioning the package to be analyzed in alignment with the probe assembly. The probe assembly has a flow path extending from the tip portion for withdrawing a sample to be analyzed from the package and an analysis unit is connected to the flow path for analyzing the sample of contents withdrawn from the package.

In preferred embodiments, the alignment structure includes an invertible spring biased alignment member that has a cylindrical inner surface and an inwardly directed support lip at one end of the cylindrical surface for supporting and positioning a cylindrical package to be analyzed, and that is disposed within a spring biased sleeve. The sleeve biasing spring resists deflection due to the weight of the package to be analyzed, while the member biasing spring is weaker than the sleeve biasing spring and allows the weight of the package to be analyzed to deflect the alignment member towards the support surface. This alignment structure facilitates accurate alignment and positioning of both cans and bottles for puncturing and analysis of their contents in a simple and easy to operate manner.

In accordance with another feature of the invention, the probe assembly includes a first flow passage extending to the puncturing tip for flowing a pressurizing medium (such as carbon dioxide) through the probe into the package on the support, and a second flow passage having a port spaced from the end surface of the tip for flowing a sample of material contained in said package to the analysis unit. There is a valve in each flow passage, and a probe insertion control controls the insertion of the probe assembly into the package a distance such that the volume of the package contents displaced by the inserted probe assembly is substantially equal to the volume of the flow passages between the puncturing tip and the valves. A temperature sensor is housed in the puncturing tip, and a pressure sensor is in the second flow passage between its port and its valve. In a beverage analyzer, the analysis unit includes a cuvette connected to the second flow passage with a flowmeter and another valve downstream from the cuvette to provide suitable flow conditions during the analysis and to maintain pressure on the cuvette between analyses. An oxygen sensor is coupled to the cuvette for measuring the concentration of oxygen in the packaged beverage. In a particular embodiment, the puncturing tip is housed in retractable sheath structure that includes a seal member for engaging and sealing the surface of the package wall to be punctured.

Analyzers in accordance with the invention permit rapid and accurate monitoring of contents of sealed packages in routine and simple manners that are independent of operator experience. In an analyzer designed for brewery applications (the analyzer being made entirely of stainless steel and non-corrosive components), the operator need merely insert the package to be analyzed, close the door, record the results, and then open the door and remove the empty package—an analysis sequence of about one minute duration.

Other features and advantages of the invention will be seen as the following description of particular embodiments progresses, in conjunction with the drawings, in which.

DESCRIPTION OF PARTICULAR EMBODIMENT

Figure 1:
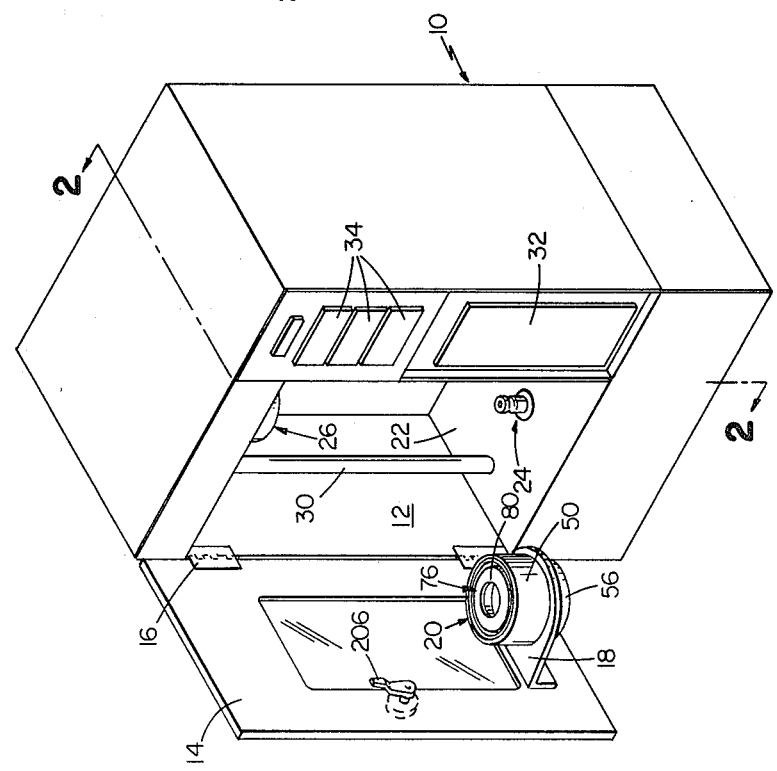
FIG. 1 is a perspective view of apparatus in accordance with the invention for analyzing the contents of packaged beverages.

Shown in FIG. 1 is a packaged beverage analyzer unit 10 that has an analysis compartment about sixteen inches in height, ten inches in width, and eight inches in depth. The front wall of compartment 12 is bounded by access door 14 that is secured to unit 10 by hinges 16. Mounted in door 14 by means of bracket 18 is support and alignment structure 20 designed to receive either cans or bottles for analysis. Projecting upwardly through floor 22 of compartment 12 is the upper end of probe assembly 24. Disposed at the top of compartment 12 above and in alignment with probe assembly 24 is pusher assembly 26 of a drive unit 28 that is mounted for reciprocation along vertical guide rails 30. The analyzer also includes an oxygen sensor assembly 32 and outputs 34 that display temperature, dissolved oxygen, and carbon dioxide values.

Figure 2:
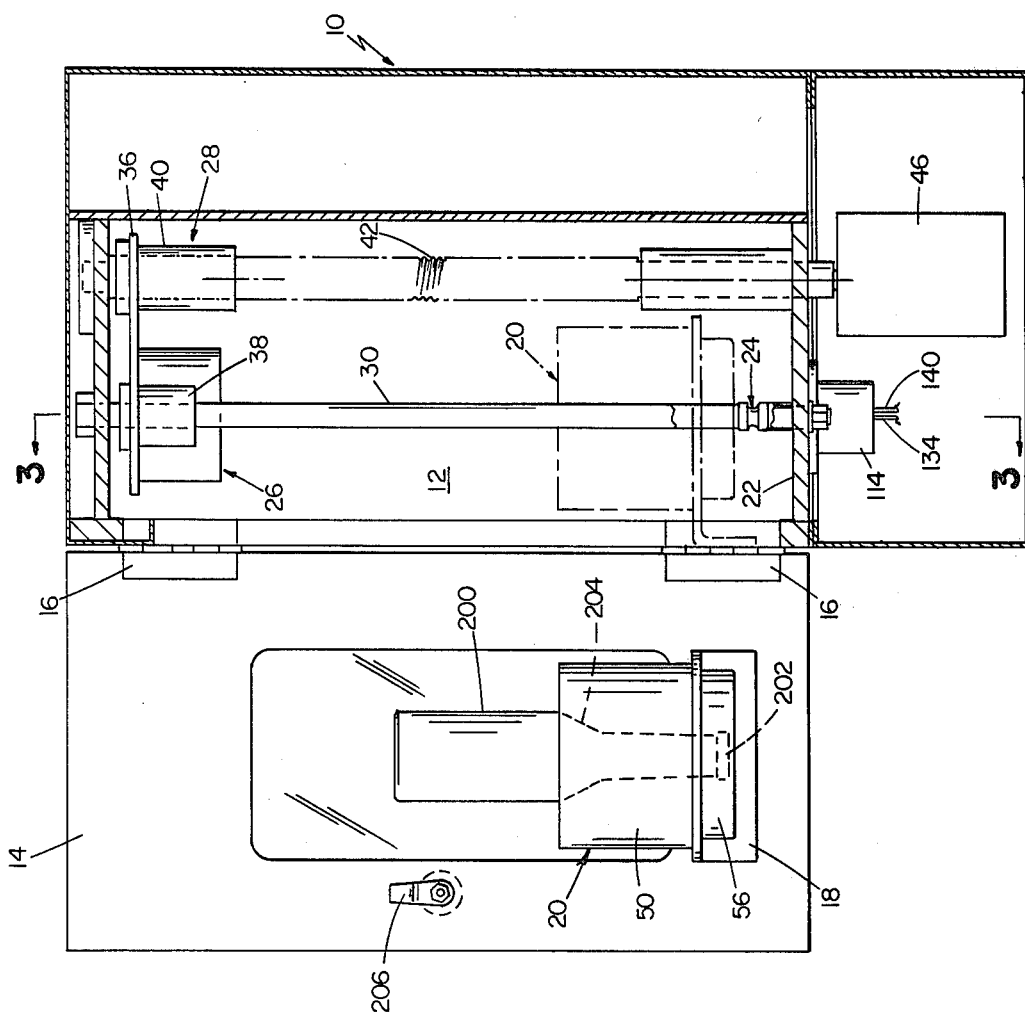
FIG. 2 is a sectional view taken along the line 2—2 of FIG. 1.

Further details of the analyzer may be seen with reference to FIG. 2. Container alignment and support structure 20 is movable between the position shown in full line in FIG. 2 when door 14 is open and the position shown in dashed line when door 14 is closed. With door 14 closed, alignment and support structure 20 is positioned in axial alignment between probe assembly 24 and pusher assembly 26. The drive unit 28 includes a support plate 36 which is guided for vertical movement along guide rods 30 by bushings 38, and carries ball nut 40 which is driven by lead screw 42. Drive unit 46 rotates lead screw 42 to lower and raise pusher assembly 26.

Figure 4:
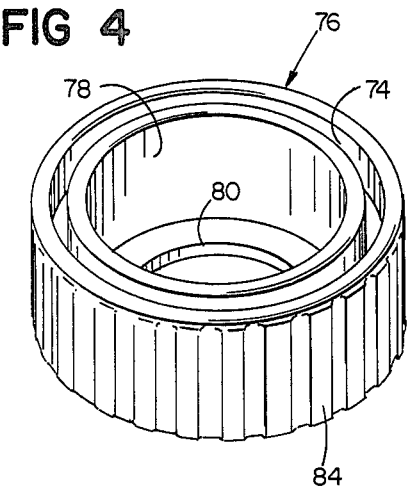
FIG. 4 is a perspective view of a component of the container alignment structure employed in the analyzer of FIG. 1.

The container support and alignment assembly mounted on bracket 18 includes a cylindrical sleeve 50 that is about 4½ inches in diameter and 3½ inches in height and includes a lower out-turned flange 52 seated on support bracket 18 and an upper in-turned flange portion 54. Telescopingly disposed within sleeve 50 is an inner sleeve 56 that has an inner diameter of about 3¾ inches and a height of about 4½ inches. Biasing spring 58 is disposed between sleeves 50 and 56, is seated on bracket 18, and acts against upper flange 60 to position flange 60 against flange 54 with the lower portion of sleeve extending downwardly through the aperture 62 in support bracket 18. Support platform 64 is seated on in-turned lip 65 of sleeve 56 and defines central aperture 66 about ⅞ inch in diameter, a support lip 68 for receiving the cap of a bottle whose contents are to be analyzed and a conical guide surface 70 which tapers upwardly and outwardly at an angle of about 35 degrees to the vertical from an inner diameter of about 1⅛ inches at its lower inner periphery to a diameter of about 1¾ inches at its upper inner periphery. Seated on platform 64 is the lower end of a spring 72 that is much weaker than support spring 58 and has a diameter of about 3¼ inch. The upper end of spring 72 is received in recess 74 of alignment member 76 that is molded of acetal resin. Member 76 (shown in FIG. 4) has an overall height of about 1¼ inches, a diameter of about 3¾ inches, an inner cylindrical wall 78 of about 2⅝ inches diameter, and an inwardly extending lip 80 from the upper end of wall 78 that defines an opening that is slightly less than two inches in diameter. Alignment member 76 has an annular recess 82, 3/16 inch in width and ½ inch in depth similar to recess 74 which permits alignment members to be inverted such that the upper end of spring 72 is received in annular recess 82.

The pusher assembly 26 includes a cylindrical pusher member 90 of cast polyurethane that is about three inches in diameter, about 1½ inches in height, and has a cylindrical inner surface 92 that defines a cylindrical recess about 1½ inches in diameter. Pusher member 90 is secured to pusher plate 94 by bolts 96. Disposed in a radial slot in the annular wall of pusher member 90 is a switch unit 98 that is secured by bracket 100 to pusher plate 94 and that has an actuator leaf 102 that extends radially inward into the recess defined by cylindrical wall 92. Pusher plate 94 is in turn secured to drive plate 36 by bushing 104 and bolt 106, the aperture in pusher plate 94 being ⅛ inch larger in diameter than the body of bushing 104 to afford a degree of tilting freedom to pusher body 90 to permit the lower surface of pusher 90 to conform to the upper surface of the container disposed in the support and alignment assembly 20.

The probe assembly 24 includes a cylindrical piercing member 110 that is seated on boss 112 of housing 114 and that housing is secured to the lower surface of plate 22 by bolts 116. Mounted in housing 114 is a piston member 118 that is biased upwardly by spring 120. Carried by piston 118 is a guide bushing 122 that slides along the body of member 110 and a resilient seal member 124 that is received on member 110 and functions as a sheath to house the piercing tip 130 of member 110. Disposed within housing 114 is limit switch 126 which is actuated by downward movement of sheath piston 118 and has leads 128. Extending downwardly from member 110 are leads 132 of a temperature sensor, a tube 134 connected to a source of carbon dioxide 136 via solenoid controlled valve 138 and a second tube 140 connected via T-fitting 142 to line 144 to which is connected pressure sensor 146, valve 148, sensing cuvette 150 of the oxygen analyzer 32 flow meter 152, and valve 154 to drain; and to line 156 which is connected through valve 158 to drain.

Figure 6:
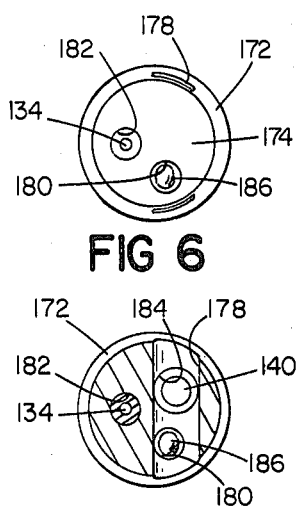
FIG. 6 is a top view of the probe assembly shown in FIG. 5.
Figure 7:
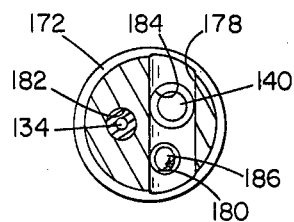
FIG. 7 is a sectional view through the probe tip taken along the line 7—7 of FIG. 5.
Figure 5:
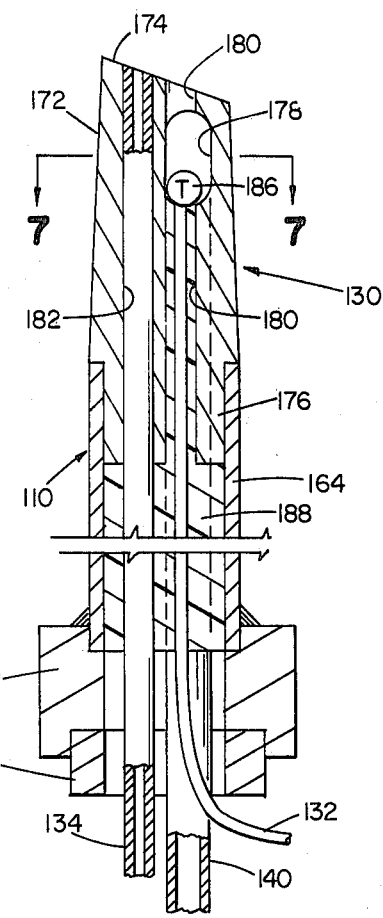
FIG. 5 is an enlarged sectional view of the probe assembly.

Further details of the piercing needle 110 may be seen with reference to FIGS. 5-7. The probe 110 includes a base 160 is ½ inch in diameter and ¼ inch high with a ⅜ inch diameter seat portion 162 and a tube 164 three inches in length and 0.31 inch in diameter. Piercing tip 130 (hardened to 50-55 $R_c$ after machining) is received and seated to the upper end of tube 164. The conical outer surface 172 of tip 130 is polished and tapers at an angle of 2½ degrees, and the upper surface 174 is inclined at an angle of 20 degrees. Tip 130 has an overall length of 0.8 inch and its shank portion 176 has a length of 0.2 inch and is ¼ inch in diameter. Machined in tip is a transverse aperture 178 that has a height of about 0.18 inch and a width of about 0.09 inch, and three axially extending bore passages 180 (0.06 inch diameter), 182 (0.06 inch diameter), and 184 (0.086 inch diameter). Bore 184 terminates at the base of transverse aperture 178 while bores 180 and 182 extend through tube surface 174. Press fitted into bore 182 is stainless steel tube 134 and press fitted into bore 184 is stainless steel tube 140. Seated in the base of aperture 178 with leads 132 extending down through bore 180 is temperature sensing thermistor 186. After shank 176 of tip 130 is seated in tube 164, the remainder of tube 164 is filled with epoxy resin 188 and then the lower end of tube 164 is silver soldered to base 160.

Figure 3:
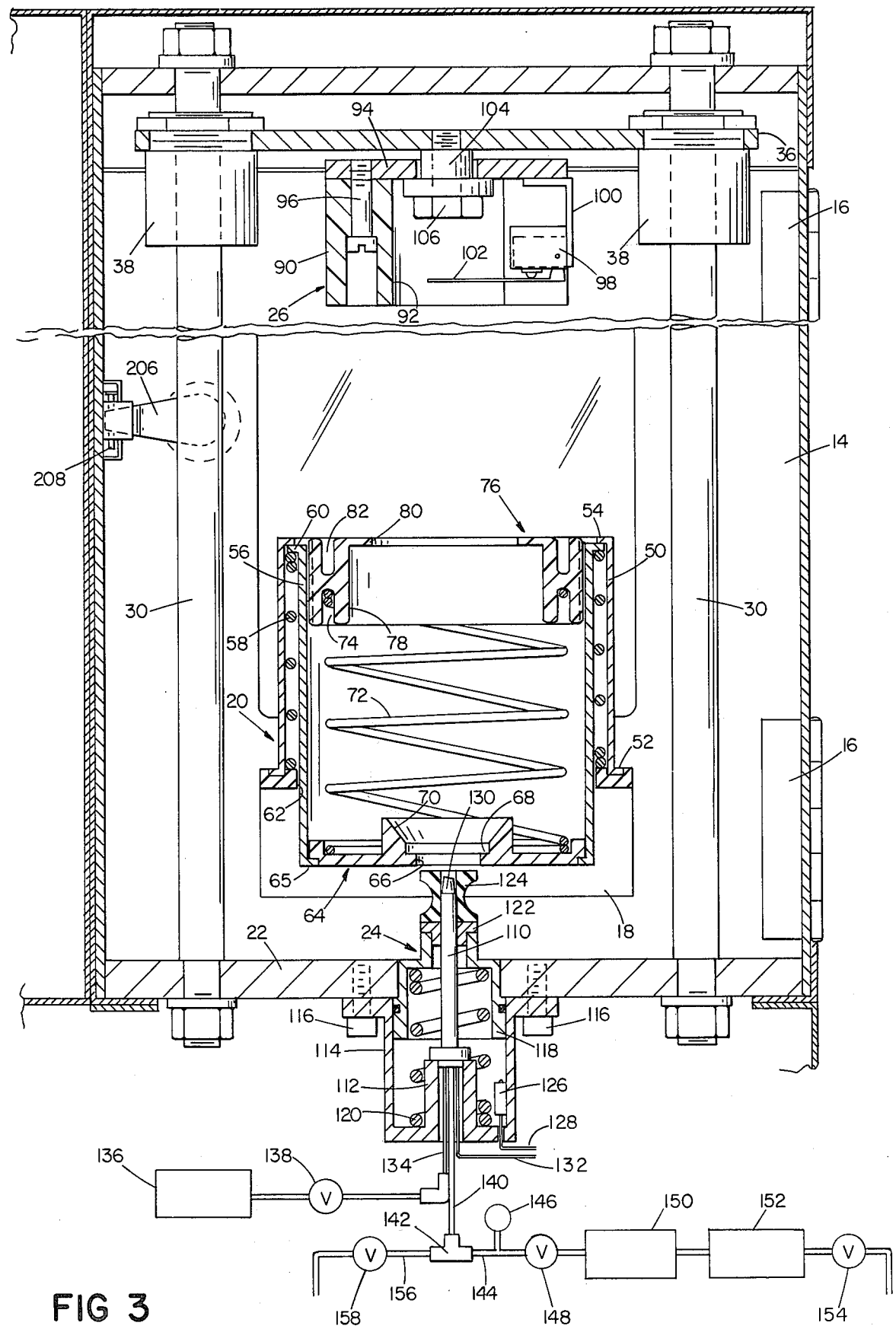
FIG. 3 is a sectional view taken along the line 3—3 of FIG. 2, showing the container support in its position with the access door closed.

In operation, when a necked container such as a bottle of beer 200 is to be analyzed alignment member is positioned as shown in FIG. 3 (with lip 80 in the high position) and bottle 200 is inserted into support assembly 20 in inverted position, as indicated in FIG. 2. In that position, the tapered neck 204 of the bottle 200 engages lip 80 of alignment member 76, with the bottle neck 204 depressing alignment member 76 against the relatively weak force of spring 72 and the bottle cap 202, as guided by conical surface 70 is centered and seated on support lip 78 while bottle neck 204 is similarly centered by lip 80. This bottle alignment arrangement accommodates a wide range of bottle shapes as the axial displacement of member 76 is a function of the shape and length of the bottle neck. In this position, the bottle 200 is supported in aligned vertical inverted position. Access door 14 is then closed, and rotation of latch 206 closes switch 208 (FIG. 3) which initiates an automated piercing and analysis sequence.

Figure 8:
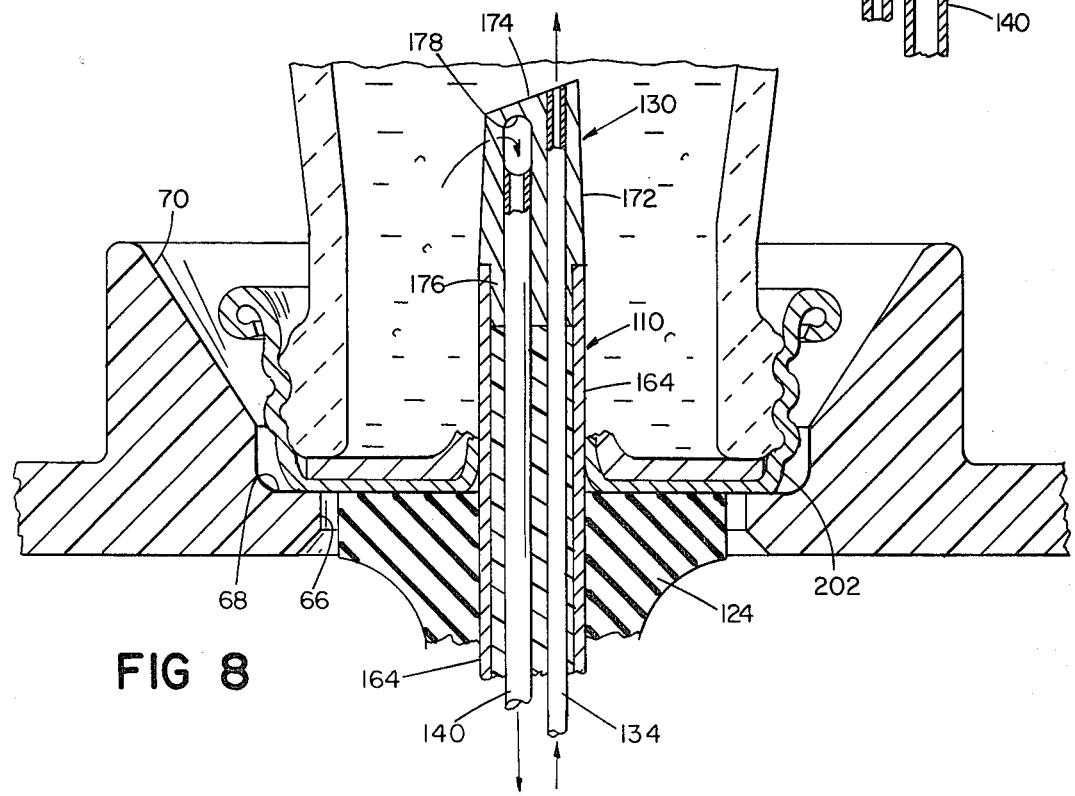
FIG. 8 is a diagrammatic view showing the probe assembly after a bottle cap has been pierced with the apparatus shown in FIGS. 1-3.
Figure 9:
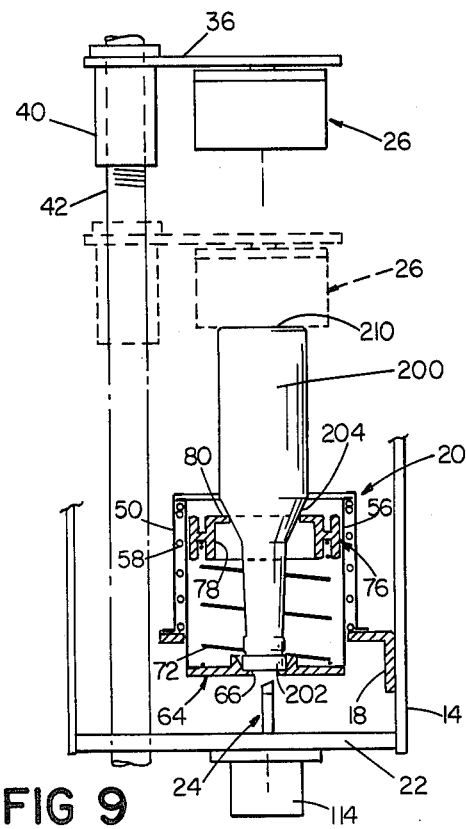
FIGS. 9-12 are diagrammatic views showing aspects of the operation of the packaged beverage analyzer of FIG. 1.

Drive motor 46 is energized to rotate lead screw 42, moving pusher assembly 26 downwardly into engagement with the bottom surface 210 of bottle 200, as shown in FIG. 9. Further rotation of lead screw 42 moves pusher assembly 26 downwardly and carries the supported bottle and support plate 62 downwardly against the force of support spring 58 and compressing that spring so that support aperture 66 is moved past the upper end of seal 124 and the upper surface of seal 124 is seated against bottle cap 202. Further downward movement compresses seal 24 and then moves the sheath assembly 118 downwardly against the further resistance of sheath biasing spring 120. As the sheath assembly is moved downwardly, the puncturing tip 130 is exposed and the bottle cap 202 is driven downwardly through the fixed puncturing needle surface 174 in a puncturing action to the position shown in FIG. 8. The volume of the probe inserted into bottle 200 is controlled to equal the volume of the fluid passages 134 and 140 to valves 138, 148 and 158 by sensor 126 or other appropriate means and signalled over leads 128 to the system controller (not shown).

Figure 10:
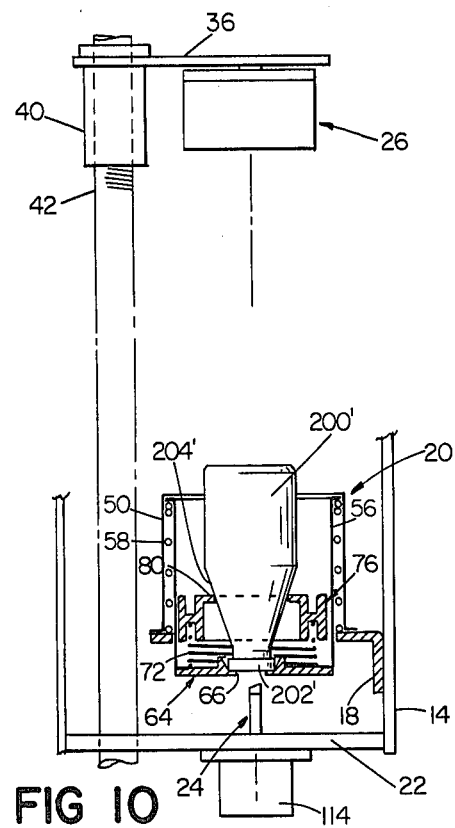
Figure 11:
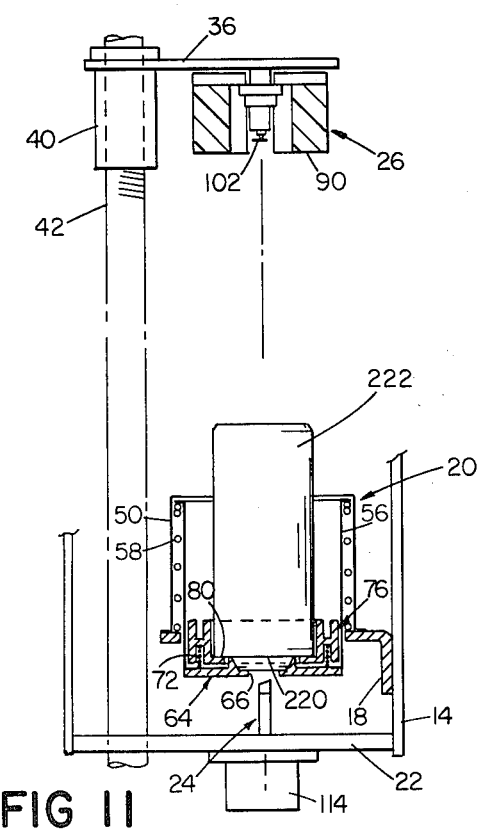

In this position as shown in FIG. 8, seal 124 is firmly seated against cap 202 and the tip 130 of probe assembly 24 is disposed within bottle 200 so that thermistor 186 senses the temperature of the beer and pressure sensor 146 senses the pressure, and those measured values are displayed at outputs 34. After five seconds, valve 138 is opened and the headspace of bottle 200 is pressured by $CO_2$ through line 134 to approximately fifteen psi over normal container pressure, then valve 148 is opened followed by valve 154 to slowly flow beer (a flow rate of about 300 milliliters per second being provided by flow meter 152) through tube 140 to the oxygen sensing cuvette 150 where the dissolved oxygen content is measured and displayed. Flow meter 152 provides a large pressure drop and maintains an overpressure on the beer in cuvette 150 to preclude foaming in cuvette 150 and also preclude false and/or variable readings from the sensor electrode. The outputs 34 are locked thirty seconds after the analysis sequence has been initiated by closure of switch 126, cuvette valve 154 is closed followed by cuvette valve 148 (so that pressure is maintained in cuvette 150), and waste valve 158 is opened to flush the beer from bottle 200 through line 140 to the drain. When a pressure drop in flush line 140 is detected, the $CO_2$ valve 138 is closed, completing the analysis sequence.

Where the beverage container is a can, alignment member 76 is inverted with springs 72 being received in recess 82 (as shown in FIG. 11). Alternatively, sleeve 56 with base 64, spring 72 and alignment member 76 may be removed and an alternate can alignment member substituted. In either event, the base 220 of can 222 is located in aligned position above probe assembly 24; and when access door 14 is secured by latch 206, an analysis sequence as above described is initiated with the can base first being sealed and then the sheath pressed downwardly and the base 220 of can 222 punctured to allow analysis of its contents. FIG. 10 shows the operation of the alignment subassembly with a bottle 200' that has a stubby neck, the alignment member 76 being depressed further than with bottle 200 with bottle 200' being similarly securely supported in aligned position for an analysis sequence.

Figure 12:
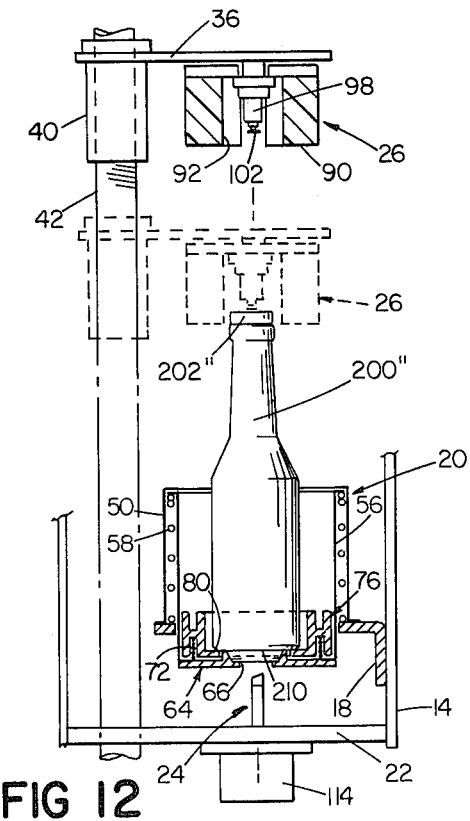

The safety interlock operation of switch 98 which operates if a bottle is inserted into support assembly 20 in upright position, is illustrated in FIG. 12. In that case, as pusher assembly 26 is driven downwardly, the neck of bottle 200" enters recess 92 and moves actuator leaf 102 to trip switch 98 and stop drive motor 46 before driving force is exerted against bottle 200" to drive the bottle and support assembly 20 downwardly towards probe assembly 24.

The analyzer permits rapid and accurate analysis of the contents of sealed packages in an automated manner in an analysis cycle of less than one minute duration.

It will be appreciated that features of the invention are applicable to analyses of the contents of other types of sealed packages. Also various modifications of the disclosed embodiments will be apparent to those skilled in the art, and therefore it is not intended that the invention be limited to the disclosed embodiment or to details thereof, and departures may be made therefrom within the spirit and scope of the invention.

What is claimed is:

1. Apparatus for analyzing the contents of a sealed package comprising
    a package alignment assembly,
    a probe assembly,
    said package alignment assembly including a support surface having an aperture therein for positioning the wall of the package to be punctured in alignment with said probe assembly, and alignment structure resiliently supported in spaced relation to said support surface for positioning the package to be analyzed in alignment with said probe assembly,
    said probe assembly having a puncturing tip portion for puncturing the wall of a package on said support surface and a flow path extending from said tip portion for withdrawing a sample to be analyzed from said package,
    a drive for causing relative motion of said probe assembly and said package support surface towards one another to cause said puncturing tip portion to penetrate the wall of a sealed package on said support surface, and
    an analysis unit connected to said flow path for analyzing the sample of the contents withdrawn from said package.

2. The apparatus of claim 1 wherein said alignment structure includes a spring biased alignment member that has an initial position spaced above said support surface, said alignment member having an opening aligned with and larger than the aperture in said support surface such that a portion of the package will extend through said opening with said wall to be punctured supported on said support surface such that said alignment member engages and supports the package in position between said probe and said drive with the package surface to be punctured positioned over said aperture.

3. The apparatus of claim 2 wherein said alignment structure includes a spring biased sleeve in which said spring biased alignment member is disposed, the sleeve biasing spring having sufficient strength to resist deflection due to the weight of the package to be analyzed, and the member biasing spring being weaker than said sleeve biasing sleeve such that the weight of the package to be analyzed deflects said alignment member towards said support surface.

4. The apparatus of either claim 2 or 3 wherein said alignment member includes axially extending guide surfaces and an inwardly directed support lip at one end of said guide surfaces for supporting and positioning a cylindrical package to be analyzed, said alignment member being invertible and said lip defining said opening for supporting and positioning a necked container to be analyzed.

5. The apparatus of claim 4 wherein said alignment member includes an annular body portion that has an annular spring receiving recess in each of its upper and lower surfaces for receiving said member biasing spring and an inner cylindrical surface that defines said axially extending guide surfaces, and said support lip is an annular flange that extends inwardly from one end of said inner cylindrical surface.

6. The apparatus of claim 1 wherein said package includes a puncturable closure, and said support includes guide surfaces for positioning said closure over said aperture.

7. Apparatus for analyzing the contents of a sealed package comprising
a package support,
a probe assembly,
said package support including a support surface having an aperture therein for positioning the wall of the package to be punctured in alignment with said probe assembly,
said probe assembly having a puncturing tip portion for puncturing the wall of a package on said support surface and a flow path
a first flow passage extending to said tip portion for flowing a pressurizing medium through said probe into the package on said support, and
a second flow passage extending from said tip portion for withdrawing a sample to be analyzed from said package,
a drive for causing relative motion of said probe assembly and said package support surface towards one another to cause said puncturing tip portion to penetrate the wall of a sealed package on said support surface, and
an analysis unit connected to said flow path for analyzing the sample of the contents withdrawn from said package.

8. The apparatus of claim 7 and further including a temperature sensor housed in said puncturing tip.

9. The apparatus of either claim 7 or 8 wherein said analysis unit includes a cuvette connected to said second flow passage, and further including a first valve in said first flow passage, a second valve in said second flow passage between said probe assembly and said cuvette and a third valve downstream from said cuvette for sealing said cuvette to maintain pressure thereon between analyses.

10. The apparatus of claim 9 and further including a flow meter in said second flow passage between said cuvette and said third valve.

11. The apparatus of claim 7 wherein said analysis unit includes a cuvette connected to said second flow passage, an oxygen sensor coupled to said cuvette for measuring the concentration of oxygen in the contents of the package to be analyzed, and a flow control downstream from said cuvette for controlling the flow rate of the liquid to be analyzed through said cuvette.

12. The apparatus of claim 7 and further including a seal member surrounding said puncturing tip for engaging and sealing the surface of the package to be punctured.

13. The apparatus of claim 7 and further including sheath structure for housing said puncturing tip of said probe assembly and means enabling the retraction of said sheath structure to expose said puncturing tip.

14. The apparatus of either claim 1 or 7 wherein said apparatus is a packaged beverage analyzer and said analysis unit includes a cuvette connected to said probe assembly, an oxygen sensor coupled to said cuvette for measuring the concentration of dissolved oxygen in the contents of the beverage to be analyzed, and a flow control downstream from said cuvette for controlling the flow rate of the beverage to be analyzed through said cuvette.

15. The apparatus of claim 14 wherein said probe assembly includes a puncturing tip portion and further including a temperature sensor disposed in an aperture in said tip portion below the puncturing surface of said tip portion, a flow path extends from said aperture to said cuvette, a first valve is disposed in said flow path between said aperture and said cuvette, and a second valve is disposed downstream of said cuvette for sealing said cuvette to maintain pressure therein between analyses.

16. The apparatus of claim 15 and further including sheath structure including a seal member for engaging and sealing the surface of the package to be punctured for housing said puncturing tip portion of said probe assembly and means enabling the retraction of said sheath structure to expose said puncturing tip in response to operation of said drive.

* * * * *